(12) United States Patent
Torto et al.

(10) Patent No.: US 6,762,242 B1
(45) Date of Patent: Jul. 13, 2004

(54) HYDROPHILIC SILICONE ELASTOMER MATERIAL USED IN PARTICULAR FOR IMPRESSIONS

(75) Inventors: Marco Del Torto, Solbiate Olana (IT); Fabienne Howe, Caluire (FR); Alain Pouchelon, Meyzieu (FR); Christian Pusineri, Serezin du Rhone (FR)

(73) Assignee: Rhodia Services, Saint Fons (FR)

( * ) Notice: Subject to any disclaimer, the term of this patent is extended or adjusted under 35 U.S.C. 154(b) by 0 days.

(21) Appl. No.: 09/958,209

(22) PCT Filed: Apr. 5, 2000

(86) PCT No.: PCT/FR00/00853

§ 371 (c)(1),
(2), (4) Date: Feb. 5, 2002

(87) PCT Pub. No.: WO00/61074

PCT Pub. Date: Oct. 19, 2000

(30) Foreign Application Priority Data

Apr. 9, 1999 (FR) .............................. 99 04675

(51) Int. Cl.$^7$ ................................ C08L 83/05
(52) U.S. Cl. ........................ 524/588; 528/31; 528/32; 528/12; 525/478; 106/38.2; 523/109; 118/264; 118/265; 427/220; 433/214
(58) Field of Search .............................. 528/31, 32, 12; 524/588; 525/478; 106/38.2; 523/109; 118/264, 265; 427/220; 433/214

(56) References Cited

U.S. PATENT DOCUMENTS

| 5,661,222 A | * | 8/1997 | Hare |
| 5,767,193 A | * | 6/1998 | Fujiki et al. |
| 5,955,513 A | | 9/1999 | Hare |

FOREIGN PATENT DOCUMENTS

| CA | 2 243 198 | * | 1/1999 |
| EP | 0 480 238 | | 4/1992 |
| WO | WO 96/32088 | | 10/1996 |
| WO | WO 98/58997 | | 12/1998 |

* cited by examiner

Primary Examiner—Kuo-Liang Peng
(74) Attorney, Agent, or Firm—Burns, Doane, Swecker & Mathis, L.L.P.

(57) ABSTRACT

Silicone material crosslinkable into silicone elastomer by polyaddition reactions is described. A material is provided offering a compromise between the following characteristics: fluidity (in non-crosslinked state), hydrophilicity (in non-crosslinked or crossliked state) and high mechanical properties (in crosslinked state). The following materials are added to crosslinkable silicone material: (i) a reinforcing siliceous filler in the form of a suspension obtained by subjecting the filler to a treatment in two stages by an agent providing compatibility and by operating in the presence of a polyorganosiloxane with Si-alkenyl functions; and (ii) one or more non-ionic, ionic or amphoteric surfactants. Said silicone material is particularly useful for impressions, for example dental impressions and for making pads used in pad printing techniques.

15 Claims, 1 Drawing Sheet

HYDROPHILIC SILICONE ELASTOMER MATERIAL USED IN PARTICULAR FOR IMPRESSIONS

FILED OF THE INVENTION

The field of the present invention is that of the silicone materials comprising a polyorganosiloxane (POS for short) composition, which can be crosslinked or cured into a silicone elastomer by polyaddition reactions, and a wetting agent allowing a hydrophilic character to be conferred on the said material. The applications intended for such systems are, especially, the taking of impressions and, more particularly, the taking of dental impressions within the context of producing dentures. The expression "taking of impressions" is understood to mean, in the present text, not only the operations of taking impressions of whatever object and of whatever shape, in order to produce a model made in particular of plaster, but also the operations of reproducing or duplicating models made in particular of plaster. The expression "taking of dental impressions" is understood to mean, in the present text, not only the operations in which dental impressions are taken in the mouth in order to obtain precise copies of jaws or parts of jaws which may or may not bear, totally or partly, teeth and to form plaster models, but also the duplicating operations in which plaster models of jaws or parts of jaws are reproduced in a laboratory for dentures. The intended applications also encompass, in particular, the manufacture of pads, such as those used in pad printing techniques.

The subject of the present invention is also a process for preparing the hydrophilic silicone elastomer material. The subject of the invention is also the use of the said material for taking impressions, for example dental impressions. Finally, the subject of the invention is the use of the said material for the manufacture of pads, such as those used in pad printing techniques.

BACKGROUND OF THE INVENTION

Silicone materials are widely used in these fields. This is partly due to the fact that silicone materials exhibit, on the one hand, a great diversity of chemical, mechanical and physical characteristics and, on the other hand, non-toxic, non-irritant and non-allergenic behaviour. Furthermore, silicone materials constitute poor substrates for the cultivation of microorganisms, thereby giving them remarkable properties with regard to hygiene.

The POS compositions of interest within the context of the present invention comprise at least:
  a POS(1) composition carrying Si-alkenyl functional groups which are capable of reacting by addition reactions with the Si—H crosslinking functional groups of a POS(2) composition;
  a POS(2) composition carrying Si—H functional groups which are capable of reacting with the Si-alkenyl functional groups of the POS(1) composition;
  optionally, an unreactive POS(3) composition, differing from the POS(1) and POS(2) compositions, which can be used as a diluent;
  a catalyst for catalysing the polyaddition reactions; and
  a particulate reinforcing mineral filler, generally of a silicious nature, treated with a compatibilizing agent, based especially on an organosilane or on an organosilazane, and optionally a semi-reinforcing or bulking filler.

It is known that such POS compositions, which advantageously may be in the form of two components, are crosslinkable or curable at room temperature and are particularly beneficial in the field of taking impressions, in particular dental impressions, since these compositions are endowed with flow and film-forming properties before crosslinking, making it possible to take an impression of whatever shape with excellent reproduction of the details. Moreover, these compositions can crosslink by polyaddition reactions in a few minutes at room temperature; in addition, they are non-toxic and satisfy the European pharmaceutical regulations. The crosslinking, which results in the hardening of the silicone composition, makes it possible to form moulds made of elastomers having mechanical properties, dimensional stability and thermal resistance which all comply with the desired specifications.

However, compositions for impressions based on silicone crosslinking by polyaddition reactions are intrinsically hydrophobic. Thus, when the mixed moulding compound is applied to the wet surface of teeth and gums, there may therefore be a casting defect or insufficient penetration into the hollows of the gums because of the presence of liquid residues; after crosslinking, the reproduction is therefore defective. Moreover, during the operations of duplicating the positive of the plaster impression, refractory plaster of hydrophilic character has to be poured into a mould made of hydrophobic silicone; there may be occlusion of small air bubbles because of the incompatibility between the surfaces, this occlusion resulting in defective reproduction.

These drawbacks may be practically eliminated by giving the intrinsically hydrophobic POS compositions a hydrophilic character by the use of various surfactants; thus, it has been proposed to use: in U.S. Pat. No. 4,657,959, a polyorganosiloxane with polyether functional groups; in U.S. Pat. No. 4,691,039 and U.S. Pat. No. 4,752,633, an ethoxylated silane; in U.S. Pat. No. 5,064,891, a polyorganosiloxane with polyol functional groups; in EP-A-0,480,233, a poly(alkoxylated) fatty alcohol; and, in FR-A-2,600,886, a water-soluble protein combined if necessary with a nonionic surfactant.

Continuing research in this field of the art, the Applicant has found:
  that the introduction of one or more surfactants into a polyaddition POS composition, containing a filler consisting, entirely or partly, of a treated reinforcing mineral filler,
  results in the development of a thixotropic character, that is to say in a significant increase in the viscosity of the silicone material in the uncrosslinked state comprising, as constituent elements, the POS composition and the surfactant(s); the silicone material consequently becomes insufficiently flowable and this drawback is of the kind to cause considerable trouble in the operations of taking impressions and to degrade the quality of the reproduction of the details.

This thixotropy phenomenon, connected with the introduction of surfactant(s) into the POS compositions with treated reinforcing mineral fillers, manifests itself particularly adversely in the case of silicone materials whose content of treated reinforcing mineral filler is high, for example equal to or greater than about 15% with respect to the weight of the silicone material. This limit of about 15% can be lowered to about 10% when the silicone material also includes a semi-reinforcing or bulking filler in an amount of 10% to 30% with respect to the weight of the silicone material.

SUMMARY OF THE INVENTION

It has now been found that it is possible to get round this difficulty by using, for preparing the silicone material, a particular treated reinforcing mineral filler, which is in the form of a suspension obtained by carrying out a two-stage treatment of the filler with a compatibilizing agent (CA for short) and by performing this treatment in the presence of at least one portion of the POS(1) composition carrying Si-alkenyl functional groups.

The combination of the use of the reinforcing mineral filler treated in a particular way, indicated above, and the use of one or more surfactants results in a polyaddition silicone material, especially one that can be used for taking impressions, providing a compromise between the following desired characteristics: fluidity (in the uncrosslinked state) and hydrophilicity (both in the uncrosslinked and the crosslinked state) and high mechanical properties (in the crosslinked state).

DESCRIPTION OF PREFERRED EMBODIMENTS

Figure 1:
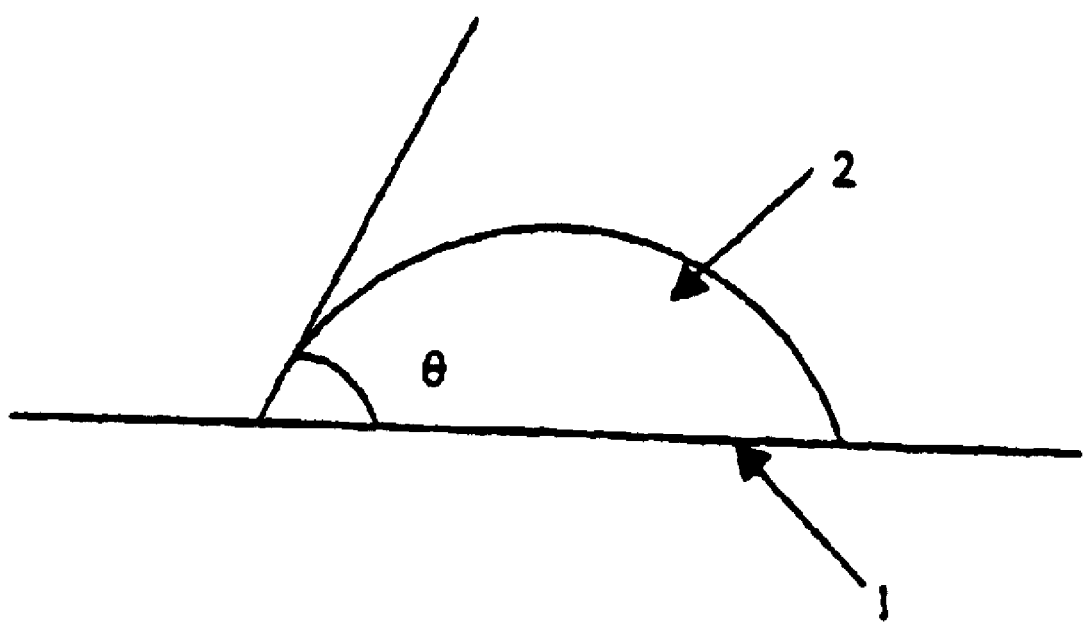
FIG. 1 is a representation of a test used to measure the hydrophilicity of a cross-linked silicone elastomer.

Thus, the present invention, according to its first subject-matter, relates to a silicone material, usable especially for taking impressions, for example dental impressions, which comprises the following constituents:

I. a POS composition crosslinkable by polyaddition reactions comprising:
  (1) at least one POS composition carrying Si-alkenyl functional groups which are capable of reacting by addition reactions with the Si—H crosslinking functional groups of a POS(2) composition,
  (2) at least one POS composition carrying Si—H functional groups which are capable of reacting with the Si-alkenyl functional groups of the POS(1) composition,
  (3) optionally, at least one unreactive POS composition, differing from the POS(1) and POS(2) compositions, which can be used as a diluent,
  (4) a catalyst for catalysing the polyaddition reactions,
  (5) a particulate reinforcing mineral filler treated with a compatibilizing agent (CA);

II. a wetting agent consisting of one or more surfactants allowing the surface of the silicone material to be given a hydrophilic character;

the said silicone material being characterized in that the filler constituent (5) is employed, during preparation of the POS composition, in the form of a suspension obtained:

by bringing the reinforcing mineral filler into contact with the compatibilizing agent (CA) and with a silicone oil comprising some or all of the POS(1) composition(s) and optionally with water;

this contacting operation being a treatment consisting in introducing the CA in two steps into the medium for preparing the suspension:
  on the one hand, before and/or more or less simultaneously with the incorporation, into at least part of the silicone oil employed and into the water optionally present, of the particulate reinforcing mineral filler used, this introduction of CA (portion 1) being performed in one or more steps with a CA fraction corresponding to a proportion of less than or equal to 8% by weight with respect to the particulate reinforcing filler; and
  on the other hand (portion 2), after this incorporation of the reinforcing filler, into at least part of the silicone oil and into the water optionally present.

To prepare the suspension of the particulate reinforcing mineral filler (5) treated using a CA, in a silicone oil, the procedure employed is as described in document WO-A-98/58997 to which a person skilled in the art may refer for further details, the said document being entirely included in the present application by reference.

The particulate reinforcing filler normally used consists of a silicious filler. As silicious fillers that can be used, all precipitated or pyrogenic silicas known to those skilled in the art are suitable. Of course, it is also possible to use cuts of various silicas.

Preferred precipitation silicas and/or pyrogenic silicas are those having a BET specific surface area of greater than 40 $m^2/g$, and more precisely between 50 and 300 $m^2/g$. More preferably, pyrogenic silicas having the abovementioned specific surface area characteristics are used. Even more preferably, pyrogenic silicas having a BET specific surface area of between 170 and 230 $m^2/g$ are used. In general, this reinforcing filler has an average particle size of less than 0.1 $\mu m$.

The compatibilizing agent of portion 1 is chosen from molecules which meet at least two criteria:
  such a molecule exhibits strong interaction with the reinforcing mineral filler, via its hydrogen bonds with itself, and with the surrounding silicone oil;
  such a molecule, or its degradation products, is easily removed from the final mixture by heating under vacuum or in a stream of gas; low molecular weight compounds are therefore preferred.

The agent of portion 1 may, for example, be:
  an organosilazane and/or a cycloorganosilazane; these may be compounds such as hexamethyldisilazane, 1,3-divinyl-1,1,3,3-tetramethyldisilazane, hexamethylcyclotrisilazane, octamethylcyclotetrasilazane and mixtures of these compounds; hexamethyldisilazane (HMDZ), possibly combined with 1,3-divinyl-1,1,3,3-tetramethyldisilazane, is preferred;
  a difunctional, or preferably monofunctional, hydroxylated siloxane;
  an amine, such as ammonia or an alkylamine of low molecular weight, such as diethylamine; and
  an organic acid of low molecular weight, such as formic acid or acetic acid.

The compatibilizing agents of portion 2 may be chosen from the various silazanes mentioned above, taken by themselves or as mixtures thereof; hexamethyldisilazane, possibly combined with divinyltetramethyldisilazane, is preferred.

As indicated in the document WO-A-98/58997, the preparation of the suspension may consist:
  in mixing:
    (100-v) parts by weight of silicone oil comprising at least one portion of the POS(1) composition(s),
    0 to 5 parts by weight of water,
    20 to 80 parts by weight of particulate reinforcing mineral filler and
    CA portion 1 representing at most 8% by weight of the reinforcing filler;
  in introducing CA portion 2 into the mixture;
  in allowing reaction to take place, preferably with stirring;
  in heating the mixture obtained, choosing a pressure/temperature pair such that devolatilization of at least some of the water optionally present and of the volatile elements occurs;

in cooling the devolatilized mixture, if necessary; and where appropriate, in adding the rest of the silicone oil (v parts by weight, the symbol v ranging from 0 to 50 parts by weight).

The mixing operation is carried out at standard temperature and pressure, and preferably in an inert atmosphere ($N_2$). It is also appropriate, under these conditions, for the silicone oil and the water optionally present, but also the compatibilizing agent, to be in liquid form in order to facilitate the mixing.

The reinforcing mineral filler represents from 10 to 50% by weight of the suspension obtained. In practice, this filler represents around 30±10%.

Advantageously, the proportion of compatibilizing agent CA initially introduced is at most equal to 8% by weight of the reinforcing mineral filler, and preferably between 1 and 3% of the weight of the reinforcing filler. Moreover, it may be pointed out that the total amount of CA is usually between 5 and 30%, preferably between 10 and 20%, of the weight of the reinforcing mineral filler. The proportions of compatibilizing agent CA introduced, on the one hand, before and/or more or less simultaneously with the incorporation of the oil/filler mixture (portion 1) and, on the other hand, after the said incorporation (portion 2) are 5–25% (portion 1) and 95–75% (portion 2) by weight in the mixture of portions 1 and 2 of the CA, respectively.

Again advantageously, the reinforcing mineral filler (5) treated with a CA is present in the silicone material according to the invention in an amount of 5 to 30%, and preferably 10 to 25%, with respect to the total mass of the silicone material [I+II combined].

According to a preferred practical method of preparing the suspension, this comprises the following steps:
1. a mixture comprising all or some of the silicone oil, the water and the first CA fraction is homogenized;
2. the particulate reinforcing mineral filler is progressively added to the mixture obtained in step 1;
3. the mixing is continued without heating;
4. the second CA fraction is progressively incorporated into the mixture obtained in step 3;
5. the mixing is continued without heating;
6. the mixture is devolatilized, preferably by heating to a temperature $\geq 100°$ C. and preferably under reduced pressure, or in a stream of inert gas such as, for example, nitrogen;
7. optionally, the devolatilized mixture is left to cool; and
8. where appropriate, the rest of the silicone oil is added.

Apart from the use of a reinforcing mineral filler (treated with a CA) in the form of the particular suspension described above, the present invention also relates to the use of one or more surfactants allowing, in particular, the surface of the silicone material to be given a hydrophilic character.

Within the context of the present invention, the surfactants used encompass nonionic, ionic and amphoteric surfactants. Where necessary, the surfactants used will be chosen in a form which makes them compatible for coming into contact with skin and mucous membranes, particularly in the mouth; they must be non-toxic, non-allergenic and non-irritating at the levels employed.

Among nonionic surfactants, mention may especially be made of: polyalkoxylated fatty acids; polyalkoxylated alkylphenols; polyalkoxylated fatty alcohols; polyalkoxylated or polyglycerolated fatty amides; polyalkoxylated fatty amines; polymers resulting from the condensation of ethylene oxide and/or propylene oxide with ethylene glycol and/or propylene glycol; polymers resulting from the condensation of ethylene oxide and/or propylene oxide with ethylenediamine; polyalkoxylated terpene hydrocarbons; polydiorganosiloxanes having siloxyl units carrying ethylene oxide chain links and/or propylene oxide chain links; polydiorganosiloxanes having siloxyl units carrying polyol-type chain links; polyalkoxylated silanes or polysilanes; alkyl glucosides; alkyl polyglucosides; sucroethers; sucroesters; sucroglycerides; sorbitan esters; ethoxylated compounds of these sugar derivatives; and mixtures of these surfactants.

Among anionic surfactants, mention may especially be made of: alkyl benzenesulphonates, alkyl sulphates, alkyl ether sulphates, alkyl aryl ether sulphates, alkyl succinates, alkyl carboxylates, alkylated derivatives of protein hydrolysates, alkyl and/or alkyl ether and/or alkyl aryl ether ester phosphates, in which the cation is in general an alkali metal or alkalineearth metal; and mixtures of the aforementioned surfactants.

Among cationic surfactants, mention may especially be made of: trialkylbenzylammonium halides; tetraalkylammonium halides; and mixtures of these surfactants.

Among amphoteric surfactants, mention may especially be made of: alkyl betaines, alkyl dimethylbetaines, alkyl amidopropylbetaines, alkyl amidopropyldimethylbetaines and alkyl trimethylsulphobetaines; imidazoline derivatives such as alkyl amphoacetates, alkyl amphodiacetates, alkyl amphopropionates, alkyl amphodipropionates; alkyl sultaines, alkyl amidopropylhydroxysultaines; products resulting from the condensation of fatty acids and of protein hydrolysates; amphoteric derivatives of alkylpolyamines; proteins and protein hydrolysates; and mixtures of these surfactants.

The preferred surfactants are nonionic surfactants. In this preferred group, the following surfactants are very particularly suitable:

(a) polyalkoxylated $C_8$–$C_{22}$ aliphatic alcohols containing from 2 to 25 alkoxylated units, such as, for example, ethylene oxide (EO) and/or propylene oxide (PO) units;

(b) polydiorganosiloxanes having siloxyl units carrying ethylene oxide chain links and/or propylene oxide chain links; as examples, mention may be made of the surfactants of formulae I, II and III described in U.S. Pat. No. 4,657,959, the contents of which are entirely included in the present application by reference; and (c) mixtures of surfactants (a) together, mixtures of surfactants (b) together and mixtures of one or more surfactants of type (a) with one or more surfactants of type (b).

The surfactant(s) are added in an amount of at most 10% and preferably at most 5% with respect to the total mass of the silicone material [I+II combined]. Within the context of the use of the surfactants (a), (b) and (c) which are most particularly suitable, the amounts used are more precisely:

with regard to the surfactant(s) of type (a), between 0.3 and 7%, and preferably between 0.5 and 3%, with respect to the same reference; and with regard to the surfactant(s) of type (b), between 0.05 and 3%, and preferably between 0.08 and 2%, with respect to the same reference.

With regard to the other constituents used in the context of the present invention, it may be mentioned that, in the case of the silicone oil—employed in the preparation of the suspension of reinforcing mineral filler (5) treated with a CA—it is possible to use, apart from some or all of the POS(1) compositions, some of the unreactive POS(3) compositions) as defined above.

With regard to the POS(1) compositions, these are polyorganosiloxanes which have, per molecule, at least two $C_2$–$C_6$ alkenyl groups linked to the silicon, these groups being located in the chain and/or at one or both chain ends.

More specifically, the POS composition comprises:
(i) siloxyl units of formula:

$$T_a Z_b SiO_{\frac{4-(a+b)}{2}} \quad (1.1)$$

in which:
T is a $C_2$–$C_6$ alkenyl group, preferably vinyl or allyl;
Z is a monovalent hydrocarbon group, not having any action unfavourable to the activity of the catalyst and preferably chosen from alkyl groups having from 1 to 8 carbon atoms inclusive, optionally substituted with at least one halogen atom, advantageously chosen from methyl, ethyl, propyl and 3,3,3-trifluoropropyl groups, and from aryl groups and, advantageously, from xylyl, tolyl and phenyl radicals;
a is 1 or 2, b is 0, 1 or 2 and a+b is between 1 and 3, preferably between 2 and 3; and
(2i) optionally other siloxyl units of formula:

$$Z_c SiO_{\frac{4-c}{2}} \quad (1.2)$$

in which Z has the same meaning as above and c has a value of between 0 and 3, preferably between 2 and 3.

It is advantageous for this POS composition to have a viscosity of between 200 and 20 000 mPa·s and preferably between 500 and 5000 mPa·s.

Of course, in the case of a mixture of several oils (1) of different viscosity, it is the viscosity of the mixture which is taken into account.

All the viscosities involved here correspond to a dynamic viscosity parameter measured, in a manner known per se, at 25° C.

The POS(1) composition may be only formed from units of formula (1.1) or it may also contain units of formula (1.2). Likewise, it may have a linear, branched, cyclic or network structure.

Z is generally chosen from methyl, ethyl and phenyl radicals, at least 60 mol % (or 60% by number) of the radicals Z being methyl radicals.

Examples of siloxyl units of formula (1.1) are vinyldimethylsiloxyl, vinylphenylmethylsiloxyl, vinylmethylsiloxyl and vinylsiloxyl units.

Examples of siloxyl units of formula (1.2) are $SiO_{4/2}$, dimethylsiloxyl, methylphenylsiloxyl, diphenylsiloxyl, methylsiloxyl and phenylsiloxyl units.

Examples of POS(L) compositions are linear and cyclic compounds such as: dimethylvinylsilyl-terminated dimethylpolysiloxanes, trimethylsilyl-terminated (methylvinyl)(dimethyl)polysiloxane copolymers, dimethylvinylsilyl-terminated (methylvinyl)(dimethyl) polysiloxane copolymers; cyclic methylvinylpolysiloxanes.

With regard to the POS(2) compositions, these are polyorganosiloxanes which have, per molecule, at least two hydrogen atoms linked to the silicon, these Si—H groups being located in the chain and/or at a chain end.

A person skilled in the art knows well that, when the POS(1) composition has 2 alkenyl groups per molecule, the POS(2) composition must preferably have at least 3 hydrogen atoms per molecule. Conversely, when the POS(2) composition has 2 hydrogen atoms per molecule, the POS(1) composition preferably has at least 3 alkenyl groups per molecule.

The POS(2) composition is more specifically a polyorganosiloxane comprising:
(i) siloxyl units of formula:

$$H_d L_e SiO_{\frac{4-(d+e)}{2}} \quad (2.1)$$

in which:
L is a monovalent hydrocarbon group, having no action unfavourable to the activity of the catalyst and chosen, preferably, from alkyl groups having from 1 to 8 carbon atoms inclusive, optionally substituted with at least one halogen atom, advantageously chosen from methyl, ethyl, propyl and 3,3,3-trifluoropropyl groups, and from aryl groups and, advantageously, from xylyl, tolyl and phenyl radicals;
d is 1 or 2, e is 0, 1 or 2 and d+e has a value of between 1 and 3, preferably between 2 and 3; and
(2i) composition optionally other siloxyl units of average formula:

$$L_q SiO_{\frac{4-g}{2}} \quad (2.2)$$

in which L has the same meaning as above and g has a value of between 0 and 3, preferably between 2 and 3.

The dynamic viscosity of this polyorganosiloxane (2) is at least equal to 10 mPa.s and is preferably between 20 and 1000 mPa·s.

The POS(2) composition may be only formed from units of formula (2.1) or it may also include units of formula (2.2).

The polyorganosiloxane (2) may have a linear, branched, cyclic or network structure.

The group L has the same meaning as the group Z above.

Examples of units of formula (2.1) are:

$$H(CH_3)_2 SiO_{1/2}, HCH_3 SiO_{2/2}, H(C_6H_5) SiO_{2/2}.$$

The examples of units of formula (2.2) are the same as those given above for the units of formula (1.2). Examples of POS(2) compositions are linear and cyclic compounds such as:
hydrogenodimethylsilyl-terminated dimethylpolysiloxanes;
trimethylsilyl-terminated (dimethyl)(hydrogenomethyl) polysiloxane copolymers;
hydrogenodimethylsilyl-terminated (dimethyl) (hydrogenomethyl)polysiloxane copolymers;
trimethylsilyl-terminated hydrogenomethylpolysiloxanes; and
cyclic hydrogenomethylpolysiloxanes.

The ratio of the number of hydrogen atoms linked to the silicon in the POS(2) composition to the total number of groups with alkenyl unsaturation in the POS(1) composition is between 0.4 and 10, preferably between 1 and 5.

With regard to the unreactive POS(3) compositions, usable as diluents, these may advantageously be a polydiorganosiloxane such as a trialkylsilyl-terminated polydialkylorganosiloxane; trimethylsilyl-terminated polydimethylsiloxanes are preferred. The dynamic viscosity at 25° C. of the POS(3) compositions is between 10 and 5000 mPa.s and preferably between 20 and 1000 mPa.s. These POS(3) compositions, when these are employed, are present in an amount of 10 to 120 parts by weight, and preferably 20 to 100 parts by weight, per 100 parts of the POS(1) and (2) compositions.

With regard to the catalysts (4) for catalysing the polyaddition reactions, these are well known to those skilled in the art.

It is preferred to use platinum and rhodium compounds. In particular, it is possible to use complexes of platinum and of an organic product described in patents U.S. Pat. No. 3,159, 601, U.S. Pat. No. 3,159,602 and U.S. Pat. No. 3,220,972 and European patents EP-A-0 057 459, EP-A-0 188 978 and EP-A-0 190 530 and the complexes of platinum and of vinyl organosiloxanes described in patents U.S. Pat. No. 3,419, 593, U.S. Pat. No. 3,715,334, U.S. Pat. No. 3,377,432 and U.S. Pat. No. 3,814,730. The catalyst more especially preferred is based on platinum. In this case, the amount by weight of catalyst (4), calculated by weight of platinum metal, is generally between 2 and 400 ppm, preferably between 5 and 100 ppm, these being based on the total weight of the POS(1) and (2) compositions.

According to one advantageous provision of the present invention, the POS composition I of the silicone material may furthermore include one or more complementary constituents chosen from the group comprising:

(6) at least one inhibitor for the polyaddition reactions;

(7) a semi-reinforcing or bulking filler;

(8) one or more colouring agents;

(9) one or more biocides; and

(10) mixtures thereof.

The inhibitors (6) are well-known compounds. It is possible, in particular, to use organic amines, organic oximes, dicarboxylic acid diesters, acetylenic alcohols, acetylenic ketones, and vinylmethylcyclo-polysiloxanes (see, for example, U.S. Pat. No. 3,445,420 and U.S. Pat. No. 3,989,667). Acetylenic alcohols are preferred and, in this context, ethynylcyclohexanol (ECH) is a particularly preferred inhibitor. The concentration of inhibitor(s), when such is used, is at most equal to 2000 ppm and preferably between 2 and 500 ppm with respect to the total mass of the POS(1) and (2) compositions.

With regard to the fillers (7), these generally have a particle diameter of greater than 0.1 μm and are preferably chosen from ground quartz, zirconias, calcined clays, diatomaceous earths, calcium carbonate, aluminium and/or sodium silicates, aluminas, and mixtures of these species. When the fillers (7) are used, they are present in the silicone material in an amount of 5 to 50% and preferably 10 to 30% by weight with respect to the total weight of the silicone material [I+II combined].

As regards the colouring agent(s). (8), it is possible to use mineral and/or organic coloured pigments.

With regard to the biocidal agent (9) which may be used in the silicone material according to the invention, it should be noted that this is preferably chosen from the active-chlorine precursor group based on N-chlorinated compounds comprising:

chloramine B (sodium N-chlorobenzene sulphonamide);

chloramine T (sodium N-chloro-p-toluene sulphonamide);

dichloramine T (N,N-dichloro-p-toluene sulphonamide);

N-trichloromethylmercapto-4-cyclohexene-1,2-dicarboxylamide;

halazone (p-n-dichlorosulphonamide benzoic acid);

N-chlorosuccinimide;

trichloromelamine;

chloroazodin

N-chloro derivatives of cyanuric acids, preferably trichloroisocyanuric acid and/or sodium dichloroisocyanuric dihydrate;

N-chlorohydantoins, preferably 1-bromo-3-chloro-5,5'-dimethylhydantoin or 1,3-dichloro-5,5'-dimethylhydantoin;

and mixtures thereof.

This group of antiseptics corresponds substantially to the N-chloramine family which comprises derivatives of amines in which one or two of the valences of the trivalent nitrogen are substituted with chlorine. In the presence of water, the N-chloramines produce hypochlorous acid HClO or salts of this acid, such as NaClO. HClO and NaClO are active chlorinated derivatives endowed with a high bactericidal capacity, which may be exploited within the context of the silicone material according to the invention (this is particularly the case when the said material is intended for taking dental impressions in the mouth).

Advantageously, the biocidal agent (9) may be combined with at least one antiseptic auxiliary agent different from the antiseptics which work by releasing chlorine and preferably chosen from the group of formulations comprising one or more quaternary ammoniums (for example, benzalkonium chloride) and optionally at least one sequestering activator, preferably selected from metal ion complexing agents (for example, ethylenediaminetetraacetic acid or EDTA).

The concentration of biocidal agent(s), when such are used, is at most equal to 1%, preferably at most equal to 0.8% and even more preferably between 0.001 and 0.5% by weight with respect to the total mass of the silicone material [I+II combined].

The present invention also relates, according to a second subject-matter, to a process for preparing the silicone material I+II as described above. This process is characterized in that it essentially consists in mixing the following ingredients:

(A) the suspension of CA-treated reinforcing mineral filler (5), as prepared according to the process described above and explained in detail in the document WO-A-98/58997, with (B) optionally, one or more POS(1) compositions as defined above;

(C) one or more POS(2) compositions as defined above;

(D) optionally, one or more POS(3) compositions as defined above;

(E) a catalyst (4) for catalysing the polyaddition reactions;

(F) optionally, one or more inhibitors (6) as defined above;

(G) optionally, a semi-reinforcing or bulking filler (7) as defined above;

(H) optionally, one or more colouring agents (8);

(I) optionally, one or more biocidal agents (9); and (J) one or more surfactants II as defined above.

This mixture is made in a conventional manner using suitable technical means known to those skilled in the art.

According to one advantageous arrangement, it is preferable:

for the suspension (A) to be prepared in the presence of a silicone oil comprising all of the POS(1) composition(s); and for the ingredients (D) and (G) to be necessarily present.

According to a beneficial variant of this process:

the silicone material is produced in the form of a system based on two components $C_1$ and $C_2$ intended to be brought into contact with each other in order to produce an elastomer crosslinked by polyaddition reactions between the POS(1) and (2) compositions; and measures are taken to ensure that only one of the components $C_1$ and $C_2$ contains the catalyst (E) and possibly one or other of the POS(1) and (2) compositions.

According to a preferred method of implementing the variant of the process described above, measures are taken to ensure that the two components $C_1$ and $C_2$ each contain a certain amount of suspension (A), the amounts in question being, highly preferably, substantially the same.

The subject of the present invention is also the use of the silicone material I+II, as described above, for taking impressions, for example dental impressions. This use, in a preferred method of implementation, consists in taking measures to ensure that the crosslinking of the silicone elastomer is initiated by mixing the components $C_1$ and $C_2$ together, in taking the impression and in allowing the crosslinking to continue until the elastomer is sufficiently crosslinked and sufficiently hard.

According to another method of use, the silicone material I+II, as described above, is intended for the manufacture of pads such as those used in pad printing techniques, in which it is beneficial to be able to have available a material having high mechanical properties, the surface energy of which may be modulated by adding one or more surfactants, while maintaining the level of fluidity necessary for manufacturing pads by moulding. This other use, in a preferred method of implementation, consists in taking measures to ensure that the crosslinking of the silicone elastomer is initiated by mixing the components $C_1$ and $C_2$ together, in forming, by moulding, in a manner known per se, an object having the shape of the desired pad and in leaving the crosslinking to continue until the elastomer is sufficiently crosslinked and sufficiently hard.

Although the crosslinking by polyaddition reactions between the POS(1) and (2) compositions can be initiated and already developed at a temperature close to room temperature (23° C.), it is also possible to carry out the crosslinking thermally (for example by heating to a temperature ranging from 60° C. to 110° C.) and/or by electromagnetic radiation (electron beam) and/or by infrared radiation.

A clearer understanding of the invention will be gained from the example which follows and which describes the preparation of a silicone material according to the invention, together with its evaluation in terms of fluidity, hydrophilicity and mechanical properties.

EXAMPLE

1. Preparation of a Silicone Material According to the Invention, in the form of a System Based on Two Components $C_1$ and $C_2$ Intended to be Brought into Contact with Each Other in Order for an Impression to be Taken 1.1 Preparation of the Suspension of Reinforcing Mineral Filler A:

The following were introduced into a 100-litre arm mixer:

40 kg of polydimethylsiloxane oil terminated at each of the chain ends by a $(CH_3)_2ViSiO_{1/2}$ unit where Vi=vinyl, having a viscosity of 1500 mPa.s;

0.24 kg of hexamethyldisilazane; and 0.24 kg of water.

After homogenization, 14 kg of a pyrogenic silica having a specific surface area of 200 m²/g were added in stages over 100 minutes. After mixing for 60 minutes, 1.88 kg of hexamethyldisilazane were added over 60 minutes. 120 minutes later, a heating phase was started, during which the mixture was placed in a stream of nitrogen (30 m³/hour); the heating continued until 140° C. was reached, which temperature hold was maintained for 2 hours. The suspension obtained was then left to cool. This operating method was repeated twice in succession.

1.2 Preparation of Component $C_1$:

The following ingredients were introduced at 23° C. into a planetary mixer:

42.7 kg of the suspension;

21.3 kg of silicious material based on ground quartz having an average particle diameter of 3 μm, marketed under the name SILBOND Cristobalit 8000 TST; and 2.85 kg of pigmentary colouring base. This was all homogenized by stirring for 1 hour.

The stirring was then stopped and the following were added:

27 kg of polydimethylsiloxane oil terminated at each of the chain ends with a trimethylsilyl unit, having a viscosity of 50 mPa.s; and 3.75 kg of poly(dimethyl)(hydrogenomethyl)-siloxane oil terminated at each of the chain ends with a $(CH_3)_2HSiO_{1/2}$ unit, having a viscosity of 30 mPa.s and containing approximately 0.25 Si—H functional groups per 100 g of oil.

There followed further homogenization by stirring for 30 minutes.

The stirring was then stopped and, after having, when necessary, raised the temperature of the mixture to a value of less than 40° C., the following were added;

1.8 kg of a polyalkoxylated $C_{10}$–$C_{12}$ aliphatic alcohol containing approximately 4 EO units and approximately 3 PO units, marketed under the brand name ANTAROX BO 327; and 0.2 kg of a polydimethylsiloxane having approximately 8 ethylene oxide units, sold under the brand name SILWET L-77.

Further homogenization was then carried out by stirring for 30 minutes.

The stirring was then stopped and, after having, where necessary, raised the temperature of the mixture to a value of less than 40° C., 0.0004 kg of ethynylcyclohexanol was added and the mixture homogenized by stirring for 30 minutes.

Next, without stopping the stirring, the mixture was degassed at 23° C., working under a reduced pressure of $266 \times 10^2$ Pa, for 15 minutes.

1.3 Preparation of Component $C_2$:

The following ingredients were introduced at 23° C. into a planetary mixer:

45 kg of the suspension; and 23 kg of silicious material based on ground quartz having an average particle diameter of 3 μm, sold under the brand name SILBOND Cristobalit 8000 TST;

and the mixture was homogenized by stirring for 30 minutes.

Stirring was then stopped and, after having, where necessary, raised the temperature of the mixture to a value of less than 50° C., the following were added:

32 kg of polydimethylsiloxane oil terminated at each of the chain ends with a trimethylsilyl unit, having a viscosity of 50 mPa.s; and 0.04 kg of a solution in divinyltetramethyldisiloxane of a platinum complex containing approximately 10% by weight of platinum(0) possessing a divinyltetramethyldisiloxane ligand (a so-called Karstedt catalyst).

The mixture is further homogenized by stirring for 1 hour.

1.4 Preparation of the Silicone Material According to the Invention:

The material was obtained by mixing, at room temperature (23° C.), 50 parts by weight of component $C_1$ with 50 parts by weight of component $C_2$. The two-component system was crosslinked at room temperature (23° C.) after producing the mixture.

The mixture may be made either by hand in a beaker, or using a laboratory metering machine such as, for example, in a dental laboratory, the machine marketed under the name SILFEX SPENDER by Austenal Dental GmbH. In the case of taking dental impressions for example, the mixture obtained was introduced into a plastic vessel containing the model to be reproduced and the crosslinking was left to continue to its completion; after completion of the crosslinking (at the end of about 30 minutes), the model was demoulded and a silicone negative obtained. The next step consisted in pouring refractory plaster into the silicone negative for the purpose of producing a perfect copy of the original model.

2. Evaluation of the Properties of the Silicone Material According to the Invention After having performed the preparation and mixed in the components $C_1$ and $C_2$, the following initial properties were measured at 23° C.:

the viscosity: this was measured using a Brookfield viscometer as specified in the AFNOR NFT 76106 standard of May 1982;

the gel time: this time corresponds to the period over which the mixture of components $C_1$ and $C_2$ continues to exhibit fluid behaviour; after this time, the material acquires the characteristics of an elastomer;

the setting time: this corresponds to the time needed for the feel of the impression to become non-tacky and for it to become handleable.

After crosslinking, the properties of the crosslinked silicone elastomer obtained were evaluated by measuring:

on the one hand, the following mechanical properties, after 24 hours of crosslinking in an atmosphere controlled at 23° C. and at 50% relative humidity:

the Shore A hardness, denoted $H_s$ (the measurements were carried out as specified in the DIN-53505 standard), tensile strength, in MPa, denoted by TS, and elongation at break, in %, denoted by EB (the measurements were carried out as specified in the ASTM-D-412 standard), tear strength, in kN/m, denoted Tear (the measurements were carried out as specified in the ASTM-D-624 A standard);

on the other hand, the hydrophilicity, again after 24 hours of crosslinking under the conditions indicated above. The method consisted in depositing a microdrop of water on the surface of the crosslinked silicone elastomer and in measuring the contact angle θ using a photographic camera (with image enlargement) and a goniometer consisting of the apparatus marketed under the name OLYMPUS DMS 300. See FIG. 1 appended hereto, in which the label 1 represents the surface of the crosslinked silicone material, the label 2 represents the microdrop deposited on the said surface and the symbol θ represents the contact angle between the drop and the deposition surface, this angle being measured.

The angles were measured about 10 seconds after the drop was deposited and the change in this drop was monitored over a minute.

The results obtained in terms of properties are given in the following table:

| PROPERTIES | |
|---|---|
| Viscosity | 6100 mPa · s |
| Gel time | 5 minutes |
| Setting time | 14 minutes |
| $H_s$ after 30 minutes | 22 |
| $H_s$ after 24 hours | 23 |
| TS | 2.6 MPa |
| EB | 400% |
| Tear | 6.5 kN/m |
| Drop contact angle θ | 61.1° (±2.7) |

The example produced in this way shows that the silicone material according to the invention exhibits, before crosslinking, excellent fluidity marked by a dynamic viscosity significantly less than the 10 000 mPa.s limit below which the viscosity must lie.

This highly favourable rheological behaviour is accompanied by essential mechanical properties, namely a $H_s$ within the 5–50 range, a TS greater than 1.5 MPa, an EB greater than 200% and a Tear greater than 5 kN/m.

The drop contact angle usually observed in the case of hydrophobic silicone networks not containing a surfactant is around 100 to 105° and the drop does not, in general, change after it has been deposited. The silicone material according to the invention, after crosslinking, is distinguished by a pronounced hydrophilicity, with a low drop contact angle (61.1°) and with rapid spreading of the drop after it has been deposited. This change may be due to effects of species dissolving in the water, thereby reducing its surface tension, or due to molecular mobility effects at the surface of the crosslinked silicone elastomer.

This is the first time, to the knowledge of the Applicant, that such an overall combination of favourable characteristics in terms of fluidity, hydrophilicity and mechanical properties has been obtained.

According to another object, the present invention therefore also relates to a silicone material which can be crosslinked into a silicone elastomer by polyaddition reactions, the said material being able to be obtained by the process according to claim 8 or 9, characterized by the following properties, taken in combination:

before crosslinking, a dynamic viscosity of less than 10 000 mPa.s; and after crosslinking for 24 hours in a controlled atmosphere at 23° C. and 50% relative humidity:

hydrophilicity marked by a drop contact angle θ, measured as specified in the test described above, of less than 90° and preferably less than 80° and a set of mechanical properties in which the $H_s$ lies in the 5–50 range, the TS is greater than 1.5 MPa, the EB is greater than 200% and the Tear is greater than 5 kN/m.

This silicone material is especially usable for taking impressions, for example dental impressions, and for manufacturing pads such as those used in pad printing techniques.

What is claimed is:

1. Silicone material which comprises the following constituents:
   I. a POS composition crosslinkable by polyaddition reactions comprising:
      (1) at least one POS(1) composition carrying Si-alkenyl functional groups which are capable of reacting by addition reactions with the Si—H crosslinking functional groups of a POS(2) composition,
      (2) at least one POS(2) composition carrying Si—H functional groups which are capable of reacting with the Si-alkenyl functional groups of the POS(1) composition,
      (3) optionally, at least one unreactive POS(3) composition, differing from the POS(1) and POS(2) compositions,
      (4) a catalyst for catalyzing the polyaddition reactions, and
      (5) a particulate reinforcing mineral filler treated with a compatibilizing agent (CA);
   II. a wetting agent comprising one or more surfactants allowing the surface of the silicone material to be given a hydrophilic character;
   wherein the filler constituent (5) is employed, during preparation of the POS composition, in the form of a suspension obtained by the following steps:
      bringing the reinforcing mineral filler into contact with the compatibilizing agent (CA) and with a silicone oil comprising some or all of the POS(1) composition(s) and optionally with water;
      this contacting operation comprising
         (a) introducing a first portion of the CA either before or approximately simultaneously with the incorporation of the particulate reinforcing mineral filler into at least part of the silicone oil employed and into the water optionally present, wherein the first portion of CA is less than or equal to 8% by weight with respect to the particulate reinforcing filler; and
         (b) after incorporation of the reinforcing filler, adding the second portion of CA into the at least part of the silicone oil and the water optionally present.

2. The silicone material according to claim 1, wherein:
   the first portion of compatibilizing agent is selected from the group consisting of:
      an organosilazane and/or a cycloorganosilazane;
      a difunctional or monofunctional hydroxylated siloxane;
      an amine; and
      an organic acid of low molecular weight; and
   the second portion of compatibilizing agent comprises an organosilazane and/or a cycloorganosilazane.

3. The silicone material according to claim 1, wherein the surfactant is selected from the group:
   nonionic surfactants comprising: polyalkoxylated fatty acids; polyalkoxylated alkylphenols; polyalkoxylated fatty alcohols; polyalkoxylated or polyglycerolated fatty amides; polyalkoxylated fatty amines; polymers resulting from the condensation of ethylene oxide and/or propylene oxide with ethylene glycol and/or propylene glycol; polymers resulting from the condensation of ethylene oxide and/or propylene oxide with ethylenediamine; polyalkoxylated terpene hydrocarbons; polydiorganosiloxanes having siloxyl units carrying ethylene oxide chain links and/or propylene oxide chain links; polydiorganosiloxanes having siloxyl units carrying polyol-type chain links; polyalkoxylated silanes or polysilanes; alkyl glucosides; alkyl polyglucosides; sucroethers; sucroesters;

sucroglycerides; sorbitan esters; ethoxylated compounds of these sugar derivatives; or mixtures of these surfactants;

anionic surfactants comprising: alkyl benzenesulphonates, alkyl sulphates, alkyl ether sulphates, alkyl aryl ether sulphates, alkyl succinates, alkyl carboxylates, alkylated derivatives of protein hydrolysates, alkyl and/or alkyl ether and/or alkyl aryl ether ester phosphates, in which the cation is an alkali metal or alkaline earth metal; or mixtures of the aforementioned surfactants;

cationic surfactants comprising: trialkylbenzylammonium halides;

tetraalkylammonium halides; or mixtures of these surfactants;

amphoteric surfactants comprising: alkyl betaines, alkyl dimethylbetaines, alkyl amidopropylbetaines, alkyl amidopropyl-dimethylbetaines and alkyl trirnethylsulphobetaines; irnidazoline derivatives such as alkyl amphoacetates, alkyl amphodiacetates, alkyl amphopropionates, alkyl amphodipropionates; alkyl sultaines, alkyl amidopropylhydroxy-sultaines;

products resulting from the condensation of fatty acids and of protein hydrolysates; amphoteric derivatives of alkylpolyamines; proteins and protein hydrolysates; or mixtures of these surfactants.

4. The silicone material according to claim 1, wherein the POS(1) composition comprises:
   (i) siloxyl units of formula:

$$T_a Z_b SiO_{\frac{4-(a+b)}{2}} \quad (1.1)$$

in which:
   T is a $C_2$–$C_6$ alkenyl group;
   Z is a monovalent hydrocarbon group, not having any action unfavorable to the activity of the catalyst and selected from the group consisting of alkyl groups having from 1 to 8 carbon atoms inclusive, optionally substituted with at least one halogen atom, and from aryl groups;
   a is 1 or 2, b is 0, 1 or 2 and a+b is between 1 and 3; and
   (2i) optionally other siloxyl units of formula:

$$Z_c SiO_{\frac{4-c}{2}} \quad (1.2)$$

in which Z has the same meaning as above and c has a value of between 0 and 3.

5. The silicone material according to claim 1, wherein the POS(2) composition comprises:
   (i) siloxyl units of formula:

$$H_d L_e SiO_{\frac{4-(d+e)}{2}} \quad (2.1)$$

in which:
   L is a monovalent hydrocarbon group, having no action unfavorable to the activity of the catalyst and selected from the group consisting of alkyl groups having from 1 to 8 carbon atoms inclusive, optionally substituted with at least one halogen atom, and from aryl groups;

d is 1 or 2, e is 0, 1 or 2 and d+e has a value of between 1 and 3; and (2i) optionally other siloxyl units of average formula:

(2.2)

in which L has the same meaning as above and g has a value of between 0 and 3.

6. The silicone material according to claim 1, further comprising one or more complementary constituents selected from the group consisting of:

(6) at least one inhibitor for the polyaddition reactions;

(7) a semi-reinforcing or bulking filler;

(8) one or more coloring agents;

(9) one or more biocides; and

(10) mixtures thereof.

7. A method for taking impressions comprising: preparing the silicone material according to claim 1, taking an impression of an object with said silicone material, and allowing the silicone material to cure.

8. The method according to claim 7, wherein the silicone material is in two components $C_1$ and $C_2$ and crosslinking of the silicone elastomer is initiated by mixing the components $C_1$ and $C_2$ together, the catalyst (E) being in one component, taking the impression and allowing the crosslinking to continue until the elastomer is sufficiently crosslinked and sufficiently hard.

9. A method for taking dental impressions comprising molding the silicone material according to claim 1, into a shape of an object, and allowing the silicone material to cure.

10. A process for preparing a silicone material comprising the following components:

I. a POS composition crosslinkable by polyaddition reactions comprising:

(1) at least one POS(1) composition carrying Si-alkenyl functional groups which are capable of reacting by addition reactions with the Si—H crosslinking functional groups of a POS(2) composition, 2. at least one POS(2) composition carrying SiH functional groups which are capable of reacting with the Si-alkenyl functional groups of the POS(1) composition;

3. optionally, at least one unreactive POS(3) composition, differing from the POS(1) and POS(2) compositions;

4. a catalyst for catalyzing the polyaddition reactions; and 5. a suspension of a particulate reinforcing mineral filler treated with a compatibilizing agent (CA);

II. a wetting agent comprising one or more surfactants allowing the surface of the silicone material to be given a hydrophilic character;

wherein the suspension of filler constituent (5) is prepared by the following steps:

(a) introducing a first portion of the CA either before or approximately simultaneously with the incorporation of the reinforcing filler into a medium comprising at least a part of a silicone oil comprising some or all of the POS(1) composition and, optionally water, the first portion of CA being less than or equal to 8% by weight of the particulate reinforcing filler; and (b) after the addition of said reinforcing filler, adding the remainder of CA into the medium; said process comprising mixing the following ingredients:

(A) the suspension of CA-treated reinforcing mineral filler (5);

(B) one or more POS(1) compositions;

(C) one or more POS(2) compositions;

(D) optionally, one or more POS(3) compositions;

(E) a catalyst (4) for catalyzing polyaddition reactions;

(F) optionally, one or more inhibitors (6);

(G) optionally, a semi-reinforcing or bulking filler (7);

(H) optionally, one or more coloring agents (8);

(I) optionally, one or more biocidal agents (9); and (J) one or more surfactants II.

11. The process according to claim 10, wherein:

the silicone material is produced in the form of a system based on two components $C_1$ and $C_2$ intended to be brought into contact with each other in order to produce an elastomer crosslinked by polyaddition reactions between the POS(1) and (2) compositions; and measures are taken to ensure that only one of the components $C_1$ and $C_2$ contains the catalyst (E) and optionally one or other of the POS(1) and (2) compositions.

12. A silicone material which can be crosslinked into a silicone elastomer by polyaddition reactions, said material being prepared by the process according to claim 10, and having the following properties, taken in combination:

before crosslinking, a dynamic viscosity of less than 10 000 mPa.s; and after crosslinking for 24 hours in a controlled atmosphere at 23° C. and 50% relative humidity:

hydrophilicity marked by a drop contact angle θ of less than 90° and a set of mechanical properties in which the $H_s$ lies in the 5–50 range, the TS is greater than 1.5 MPa, the EB is greater than 200% and the Tear is greater than 5 kN/m.

13. A method for preparing pads employed in pad printing techniques comprising: preparing a silicone material, taking an impression of a printing pad with said silicone material, and allowing the silicone material to cure, wherein the silicone material comprises the following constituents:

I. a POS composition crosslinkable by polyaddition reactions comprising:

(1) at least one POS(1) composition carrying Si-alkenyl functional groups which are capable of reacting by addition reactions with the Si—H crosslinking functional groups of a POS(2) composition, 2. at least one POS(2) composition carrying SiH functional groups which are capable of reacting with the Si-alkenyl functional groups of the POS(1) composition;

3. optionally, at least one unreactive POS(3) composition, differing from the POS(1) and POS(2) compositions;

4. a catalyst for catalyzing the polyaddition reactions; and 5. a particulate reinforcing mineral filler treated with a compatibilizing agent (CA);

II. a wetting agent comprising one or more surfactants allowing the surface of the silicone material to be given a hydrophilic character;

wherein the filler constituent (5) is employed, during preparation of the POS composition, in the form of a suspension obtained by the following steps:

bringing the reinforcing mineral filler into contact with the compatibilizing agent (CA) and with a silicone oil comprising some or all of the POS(1) compositions(s) and optionally with water;

the contacting operation comprising:
(a) introducing a first portion of the CA either before or approximately simultaneously with the incorporation of the particulate reinforcing mineral filler into at least part of the silicone oil employed and into the water optionally present, wherein the first portion of CA is less than or equal to 8% by weight with respect to the particulate reinforcing filler; and
(b) after incorporation of the reinforcing filler, adding the second portion of CA into the at least part of the silicone oil and the water optionally present.

14. The method according to claim 13, wherein the silicone material is in two components $C_1$ and $C_2$ and crosslinking of the silicone elastomer is initiated by mixing the two components $C_1$ and $C_2$ together, the catalyst (E) being in one component, molding an object having the shape of the desired pad and allowing crosslinking to continue until the elastomer is sufficiently crosslinked and sufficiently hard.

15. A method for manufacturing pads employed in pad printing techniques comprising shaping a silicone material into a printing pad, and allowing the silicone material to cure, wherein the silicone material comprises the following constituents;

I. a POS composition crosslinkable by polyaddition reactions comprising:
(1) at least one POS(1) composition carrying Si-alkenyl functional groups which are capable of reacting by addition reactions with the Si—H crosslinking functional groups of a POS(2) composition,
2. at least one POS(2) composition carrying SiH functional groups which are capable of reacting with the Si-alkenyl functional groups of the POS(1) composition;
3. optionally, at least one unreactive POS(3) composition, differing from the POS(1) and POS(2) compositions;
4. a catalyst for catalyzing the polyaddition reactions; and
5. a particulate reinforcing mineral filler treated with a compatibilizing agent (CA);

II. a wetting agent comprising one or more surfactants allowing the surface of the silicone material to be given a hydrophilic character;

wherein the filler constituent (5) is employed, during preparation of the POS composition, in the form of a suspension obtained by the following steps:

bringing the reinforcing mineral filler into contact with the compatibilizing agent (CA) and with a silicone oil comprising some or all of the POS(1) composition(s) and optionally with water;

this contacting operation comprising:
(a) introducing a first portion of the CA either before or approximately simultaneously with the incorporation of the particulate reinforcing mineral filler into at least part of the silicone oil employed and into the water optionally present, wherein the first portion of CA is less than or equal to 8% by weight with respect to the particulate reinforcing filler; and
(b) after incorporation of the reinforcing filler, adding the second portion of CA into the at least part of the silicone oil and the water optionally present.

* * * * *